US009078806B2

(12) United States Patent
Bemer

(10) Patent No.: US 9,078,806 B2
(45) Date of Patent: Jul. 14, 2015

(54) STORAGE ASSEMBLY FOR CONTRAST MEDIA

(75) Inventor: François Bemer, Massy (FR)

(73) Assignee: GUERBET, Villepinte (FR)

( * ) Notice: Subject to any disclaimer, the term of this patent is extended or adjusted under 35 U.S.C. 154(b) by 864 days.

(21) Appl. No.: 11/662,193

(22) PCT Filed: Sep. 8, 2005

(86) PCT No.: PCT/EP2005/054471
§ 371 (c)(1), (2), (4) Date: Aug. 3, 2007

(87) PCT Pub. No.: WO2006/029989
PCT Pub. Date: Mar. 23, 2006

(65) Prior Publication Data

US 2008/0065043 A1 Mar. 13, 2008

(30) Foreign Application Priority Data

Sep. 8, 2004 (FR) ..................................... 04 09505

(51) Int. Cl.

| | |
|---|---|
| ***A61B 19/00*** | (2006.01) |
| *B65D 25/08* | (2006.01) |
| *B65D 73/00* | (2006.01) |
| *B65D 30/00* | (2006.01) |
| *B65D 30/08* | (2006.01) |
| *A01B 1/00* | (2006.01) |
| *A61J 1/10* | (2006.01) |

(52) U.S. Cl.
CPC ... *A61J 1/10* (2013.01); *B65D 73/00* (2013.01)

(58) Field of Classification Search
CPC ......... A61B 19/00; A61M 2/32; B65D 25/08; B65D 73/00; B65D 30/00; B65D 30/08
USPC .................................................. 604/408–411
See application file for complete search history.

(56) References Cited

U.S. PATENT DOCUMENTS 4,199,062 A 4/1980 Johnston et al.
4,412,834 A * 11/1983 Kulin et al. .................... 604/29

(Continued)

FOREIGN PATENT DOCUMENTS

EP 0 067 420 A 12/1982
EP 0 852 152 A 7/1998
FR 2 722 983 A 2/1996

*Primary Examiner* — Tatyana Zalukaeva
*Assistant Examiner* — Ilya Treyger
(74) *Attorney, Agent, or Firm* — Birch, Stewart, Kolasch & Birch, LLP

(57) ABSTRACT

The invention relates to a doubly packaged storage assembly (5) for an aqueous medical solution, more especially a contrast agent, comprising an overpackage (4) in which at least one flexible packaging container (3) is packaged and hermetically sealed, said container (3) being filled with an aqueous solution and sealed by means of a connector provided with a cap, in which storage assembly (5):

- the overpackage (4) comprises two superposed foils made of flexible or semi-rigid polymer materials, the first foil being transparent over its entire area and the second foil being opaque over its entire area; and
- the packaging container (3) comprises two superposed sheets made of polymer material and an access member at the distal end of which the connector and the cap are placed, the connector allowing the packaging container to be sealed after it has been filled with the aqueous solution.

25 Claims, 5 Drawing Sheets

(56) References Cited

U.S. PATENT DOCUMENTS

| | | | | |
|---|---|---|---|---|
| 5,370,221 A * | 12/1994 | Magnusson et al. | 206/221 |
| 5,728,087 A * | 3/1998 | Niedospial, Jr. | 604/408 |
| 5,896,989 A | 4/1999 | Ropiak et al. | |
| 5,910,138 A * | 6/1999 | Sperko et al. | 604/408 |
| 6,024,220 A * | 2/2000 | Smith et al. | 206/484 |
| 6,039,718 A | 3/2000 | Niedospial, Jr. | |
| 6,241,717 B1 * | 6/2001 | Niedospial, Jr. | 604/408 |
| 6,613,036 B1 | 9/2003 | Farmer et al. | |
| 6,893,428 B2 * | 5/2005 | Willemstyn | 604/533 |

* cited by examiner

STORAGE ASSEMBLY FOR CONTRAST MEDIA

The present invention relates to a storage assembly comprising a container, referred to as a "pouch", for an aqueous solution (more especially a contrast agent), a connector for connecting the pouch to a peripheral device, such as a syringe, and a package for packaging the pouch so as to protect the aqueous solution contained in the pouch from deteriorating. The invention also relates to the associated storage method.

More particularly, the invention relates to a storage assembly for a diagnostic product for medical imaging (contrast agent) and a liquid pharmaceutical formulation in which, even if the medical fluid is stored for a long period, it will not undergo any deterioration, such as loss of water, and the invention also relates to the associated storage method.

Hereafter, the container will be referred to as "pouch", the connector will be referred to as "Luer" and the package will be referred to as "overpouch".

GENERAL PRESENTATION OF THE PRIOR ART

In the medical treatment field, glass bottles and glass bulbs have been replaced with flexible plastic containers for blood products. However, in the case of contrast agents, packages of the flexible plastic pouch type have hitherto been little used, glass being largely dominant. PVC pouches are known, but they have problems, especially environmental problems. Pouches made of a material of the polypropylene type have been described, but their use has not grown, probably because of regulatory problems and/or problems of how to store these packages.

This is because such a type of container filled with parenteral fluid must have sufficient thermal resistance to allow sterilization of their contents (sterilization temperature above 100° C.). Moreover, this type of container is preferably made of a transparent material so that their content can be monitored from the outside.

When the medical fluid contained in such a container includes a component subject to deterioration, for example a light-sensitive or oxidation-sensitive component, it is known to package said container in a packaging material having good gas barrier properties, for example a material that includes a layer of polyvinyl chloride, and good ultraviolet radiation barrier properties, for example a material that includes an opaque aluminum layer.

However, with such assemblies, in order for the user to be able to check the content of the flexible container and read the identification inscriptions printed on it, it is necessary to remove the packaging material, thereby reducing the shelf life of the storage assembly.

To solve this drawback, it is known to leave one face of the packaging material transparent. The plastic container is then placed in the packaging material so that the face of said container bearing the identification inscriptions is in contact with the transparent face of the packaging material. The storage assembly thus obtained is then placed in an autoclave so as to sterilize the aqueous solution at a temperature above 100° C.

However, these assemblies have the following major drawback. When the storage assembly is subjected to a high temperature, in order to sterilize the solution contained in the plastic container, the permeability of the material making up said container increases, causing a loss of water, which undesirably condenses on the internal face of the packaging material. This makes it difficult to read the identification inscriptions printed on the flexible plastic container and results in a loss of product from the pouch through suction of the product by the dry air between the pouch and the overpouch during autoclaving. To prevent this condensation, vacuum sterilization has been attempted in the prior art, but the pouch then sticks to the overpouch, something which is unacceptable from the standpoint of presenting the product. In addition, vacuum processing involves thermoforming, a physical stress which impairs the physical properties of the overpouch and its permeability, and may cause a loss of stability.

Furthermore, more especially in the case of contrast agents (for example for an X-ray scanner or for MRI (magnetic resonance imaging)), the product administered to the patient is expensive. This means that the losses of product must be minimized.

Furthermore, it is very difficult if the packaging material is sterilized at a temperature above 100° C. to produce, with such material, a high-quality peelable coating.

Finally, the elements for sealing the access to the inside of the pouch of the storage assemblies of the prior art are not very practical for a user.

Moreover, certain manufacturers have developed very different technical solutions to avoid these various problems, such as flasks (no longer pouches) made of a rigid plastic.

One object of the present invention is to provide a storage assembly for alleviating at least one of the abovementioned drawbacks.

Moreover, the invention aims to solve other technical problems associated with the clinical use of contrast agents. Specifically, it is desired for the pouch to be able to be connected to various types of adapters and injection devices, such as manual or automatic syringe injectors or automatic injectors for pouches.

PRESENTATION OF THE INVENTION

The invention relates to a doubly packaged storage assembly for an aqueous medical solution, more especially a contrast agent, comprising an overpackage in which at least one flexible packaging container is packaged and hermetically sealed, said container being filled with an aqueous solution and sealed by means of a connector provided with a cap, in which storage assembly:

the overpackage comprises two superposed foils made of flexible or semi-rigid polymer materials, the first foil being transparent over its entire area and the second foil being opaque over its entire area; and the packaging container comprises two superposed sheets made of polymer material and an access member at the distal end of which the connector and the cap are placed, the connector allowing the packaging container to be sealed after it has been filled with the aqueous solution.

Preferred but non-limiting aspects of the storage assembly according to the invention are the following:

the connector and the cap are made of polycarbonate;

the connector comprises a cylindrical body, one inside diameter of which is approximately equal to the outside diameter of the access member so that a portion of the cylindrical body encircles and comes into contact with a portion of the access member when the connector is engaged with the access member;

the connector has an external surface in the form of part of a truncated cone;

the diameter of the external surface in the form of a truncated cone decreases from the proximal end towards the distal end of the cylindrical body the connector is of the female Luer type;

the connector includes a frangible section provided with fins extending radially outwards;

the foils of the overpackage are composed of laminated films chosen from polypropylene, polyamide and polyethylene films;

the second foil of the overpackage comprises an opaque film of the metallized polyester type;

the second foil of the overpackage comprises an opaque aluminum film;

the sheets of the packaging container are composed of laminated polypropylene films;

the first sheet includes a region having identification inscriptions, such as the name of the product, the name of the manufacturer and the amount of product contained in the container;

the superposed sheets sealed on their periphery define an internal reservoir, the upper part of the packaging container comprising a central sector, in which the sheets are sealed together and form a hole of elliptical appearance, and two symmetrically placed ovoid sectors extending outwards from the hole and sealed on their periphery in order to make the upper part less flexible than the polymer sheets that form the internal reservoir; and the superposed sheets sealed on their periphery define an internal reservoir, the lower part of the packaging container comprising two symmetrically placed ovoid sectors extending outwards from the hole and sealed on their periphery in order to make the lower part less flexible than the polymer sheets that form the internal reservoir.

The invention also relates to a method of storing an aqueous medical solution in a doubly packaged storage assembly, the method comprising the steps consisting in:

filling a packaging container with the aqueous medical solution via an access member of the packaging container;

sealing the packaging container by means of a connector;

placing a cap on the end of the connector;

placing the packaging container, the access member of which is sealed by the connector, in an overpackage comprising a transparent face and an opaque face; and sealing the overpackage so as to hermetically seal the container, the access member of which is sealed by the connector provided with the cap.

It should be noted that within the context of the present invention the step consisting in placing a cap on the end of the connector may be carried out before or after the step consisting in sealing the packaging container by means of the connector.

Preferred but non-limiting aspects of the storage method according to the invention are the following:

the step consisting in sealing the packaging container by means of a connector consists in sealing the container by means of a female Luer connector;

the method further includes, prior to the step consisting in placing the container in the overpackage, the step consisting in sterilizing the assembly comprising the packaging container, the connector and the cap of the connector, preferably by autoclaving between 100 and 150° C. for a time between 10 and 40 minutes; and the method further includes, prior to the step consisting in placing the container in the overpackage, the step consisting in sterilizing the assembly comprising the packaging container, the connector and the cap by autoclaving at a temperature of approximately 121° C. for a time of approximately 20 minutes.

The invention also relates to an overpackage comprising two superposed foils made of flexible or semi-rigid polymer materials, the first foil being transparent over its entire area and the second foil being opaque over its entire area, for a storage assembly as described above.

The invention also relates to a packaging container comprising two superposed sheets made of polymer material and an access member at the distal end of which the connector and the cap are placed, for a storage assembly as described above.

PRESENTATION OF THE FIGURES

Other features and advantages of the invention will become more clearly apparent from the following description, which is purely illustrative and non-limiting and must be read in conjunction with the appended drawings in which.

DESCRIPTION OF EMBODIMENTS OF THE INVENTION

Figure 1:
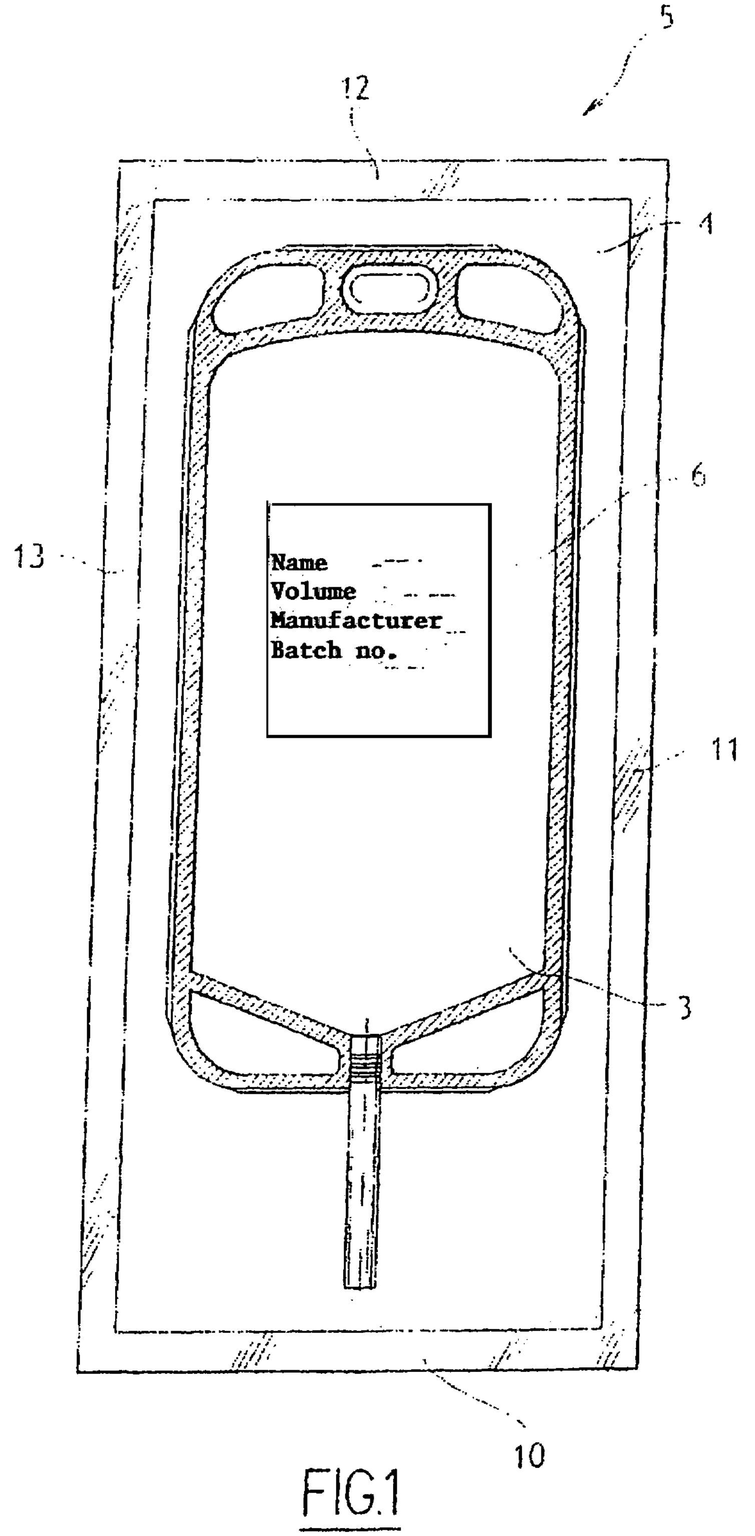
FIG. 1 illustrates a front view of a storage assembly according to the present invention.
Figure 2:
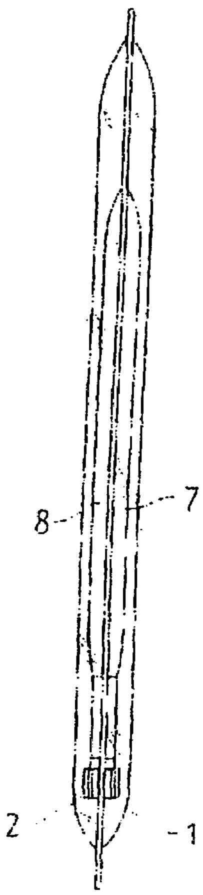
FIG. 2 illustrates a side view of the storage assembly according to the present invention.
Figure 3:
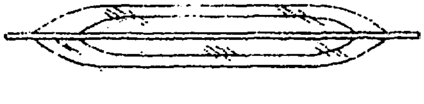
FIG. 3 illustrates a top view of the storage assembly according to the present invention.
Figure 4:
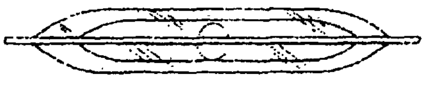
FIG. 4 is a bottom view of the storage assembly according to the present invention.

The storage assembly according to the present invention, allowing an aqueous solution such as a contrast agent or a liquid pharmaceutical formulation to be stored, will now be described in detail with reference to FIGS. 1 to 9. The equivalent elements shown in the various figures will bear the same numerical references.

The storage assembly comprises an overpouch containing a medical pouch. This medical pouch includes an access member onto which a female Luer is forcibly fitted after said pouch has been filled with a parenteral solution. The female Luer is provided with a cap.

In what follows, the description will be given as regards a user facing the storage assembly, the access member of the medical pouch being at the bottom.

The Overpouch:

FIGS. 1, 2, 3 and 4 illustrate a front view, side view, top view and bottom view of a medical pouch 3 contained in an overpouch 4.

This overpouch 4 has a generally rectangular shape. It may either be peelable or tearable. The overpouch 4 comprises two superposed foils 1, 2 of appropriate length and width.

The first and second foils 1, 2 are made of transparent, flexible or semi-rigid polymer materials. These foils 1, 2 are for example made of polyamide, polyethylene, polypropylene or a polyethylene/polypropylene copolymer.

Each of the superposed transparent foils 1, 2 preferably consist of laminated films, at least one of which is impermeable to gases, moisture and atmospheric bacteria.

The first foil 1 is left transparent over its entire area so as to allow the amount of the content of the medical pouch 3 contained in the overpouch 4 to be observed. It also allows the identification inscriptions in the region 6 of the medical pouch 3, such as the name of the product contained in the medical pouch, the volume of product contained in the medical pouch, the name of the manufacturer and the manufacturing batch number to which the medical fluid belongs, to be read.

The second foil 2 further includes an opaque laminated film having ultraviolet radiation barrier and water barrier properties, such as a metal, preferably aluminum, film (for example a metallized polyester film) heat-sealed and covering the entire area of the second foil 2. This second foil 2 protects the integrity of the light-sensitive medical fluids contained in the medical pouch 3. A contrast agent such as Xenetix® (Guerbet) for scanning typically contains 60 to 80 g of active principle depending on the concentration used.

The first and second superposed foils 1, 2 are joined together along marginal sectors 10, 11, 12 and 13.

The use of the overpouch 4 allows the shelf life of the aqueous solution contained in the medical pouch 3 to be increased, thereby complying with the European Pharmacopoeia whereby the loss of water must be less than 5% after three months of storage at 40° C.

The Applicant has discovered that, without the overpouch 4, after storage for six months the loss of water due to the permeability of the polypropylene material used for making the medical pouch 3 was too great, whereas when the above overpouch 4 is present, this water was markedly better retained. Suitable storage with a loss of the order of 1% for long periods, up to about 36 months, can be achieved.

The following table gives the results obtained using a first embodiment and a second embodiment of the overpouch 4 according to the invention:

the water permeability is low enough for the contrast agent not to be impaired despite the sterilization and the lengthy storage.

According to the invention, an overpouch will be chosen so that the foils 1, 2 have a thickness between 50 μm and 100 μm, preferably between 60 μm and 75 μm and even more preferably between 62 μm and 71 μm. This thickness provides a product that is flexible and pleasant to handle.

The Pouch:

The medical pouch 3 comprises two superposed sheets 7, 8 of appropriate length and width, and also an access member 30.

The sheets 7, 8 are made of flexible or pliant materials, such as polymer materials comprising polyethylene, polypropylene and preferably thermoplastics. The superposed sheets 7, 8 forming the medical pouch 3 are made of transparent materials or at least translucent materials so as to allow the amount of its content to be observed during the operations of storing the product and of administering it to the patient.

Each of the superposed transparent sheets 7, 8 preferably consist of several layers of thin laminated films, at least one of which constitutes a barrier that is impermeable to gases, moisture and atmospheric bacteria. Moreover, the film in contact with the aqueous solution (or parenteral solution) is preferably chemically inert and impermeable to gases. Furthermore, the film in contact with the parenteral solution must not contain toxic agents that could spread into the parenteral solution. For example, the sheets 7, 8 forming the medical pouch 3 may comprise a stack of polypropylene films (or polypropylene multilayer). In another example, the sheets 7, 8 forming the medical pouch 3 may comprise a polyvinyl chloride film inserted between two polyvinyl acetate or polyethylene films. In this example, the polyvinyl chloride film constitutes the impermeable barrier. In a preferred embodiment, the material of the pouch wall has a multilayer structure with at least 80 to 90% polypropylene or polyethylene.

For example, the pouch is formed from three, external, intermediate and internal, layers from: polypropylene

| | TECHNICAL CHARACTERISTICS | UNITS | 1ST VALUES | 2ND VALUES |
|---|---|---|---|---|
| | THICKNESS | μm | 62.00 | 71.00 |
| | WEIGHT | $g/m^2$ | 64.90 | 92.20 |
| SEALING | OUTPUT | $m^2/kg$ | 15.40 | 10.80 |
| | OXYGEN | $cc/m^2$/24 h · 23° C. 50% RH | 1.00 | 0.05 |
| | CARBON DIOXIDE | $cc/m^2$/24 h · 23° C. 50% RH | 4.00 | 0.05 |
| | NITROGEN | $cc/m^2$/24 h · 23° C. 50% RH | 0.20 | 0.05 |
| | WATER VAPOUR | $cc/m^2$/24 h · 38° C. 90% RH | 1.00 | 0.05 |
| | WELDABILITY TEMPERATURE RANGE | ° C. | Min = 165, Max = 190 | Min = 165, Max = 190 |
| | OPERATING TEMPERATURE RANGE | ° C. | Min = 2, Max = 125 | Min = 2, Max = 125 |

Thus, the overpouch 4 will have different sealing characteristics depending on its thickness and its weight. The greater the weight and thickness of the overpouch 4, the higher the water, carbon dioxide, oxygen and nitrogen impermeability of the overpouch 4.

One of the advantages of the overpouches 4, the sealing results of which are given in the above table, is that they are sufficiently impermeable to prevent the loss of water, but also sufficiently permeable to prevent undesirable condensation inside said overpouches. The composition and thickness of the overpackage and of the packaging container are such that homopolymer; propylene/ethylene/butylene copolymers; styrene/ethylene copolymers; or ethylene/carboxylic ester copolymers.

The superposed sheets 7, 8 are preferably welded together flat, so as to form a pouch 3 whose volume is zero before it is filled with parenteral solution. When the medical pouch 3 is filled or partly filled, it has the form of a bag.

Depending on the volume intended to be administered to the patient, the internal volume capacity of the pouch 3 may be 100, 150, 200 or 500 milliliters (ml). For MRI products, the volume may be reduced, for example to 30 or 50 ml.

Figure 5:
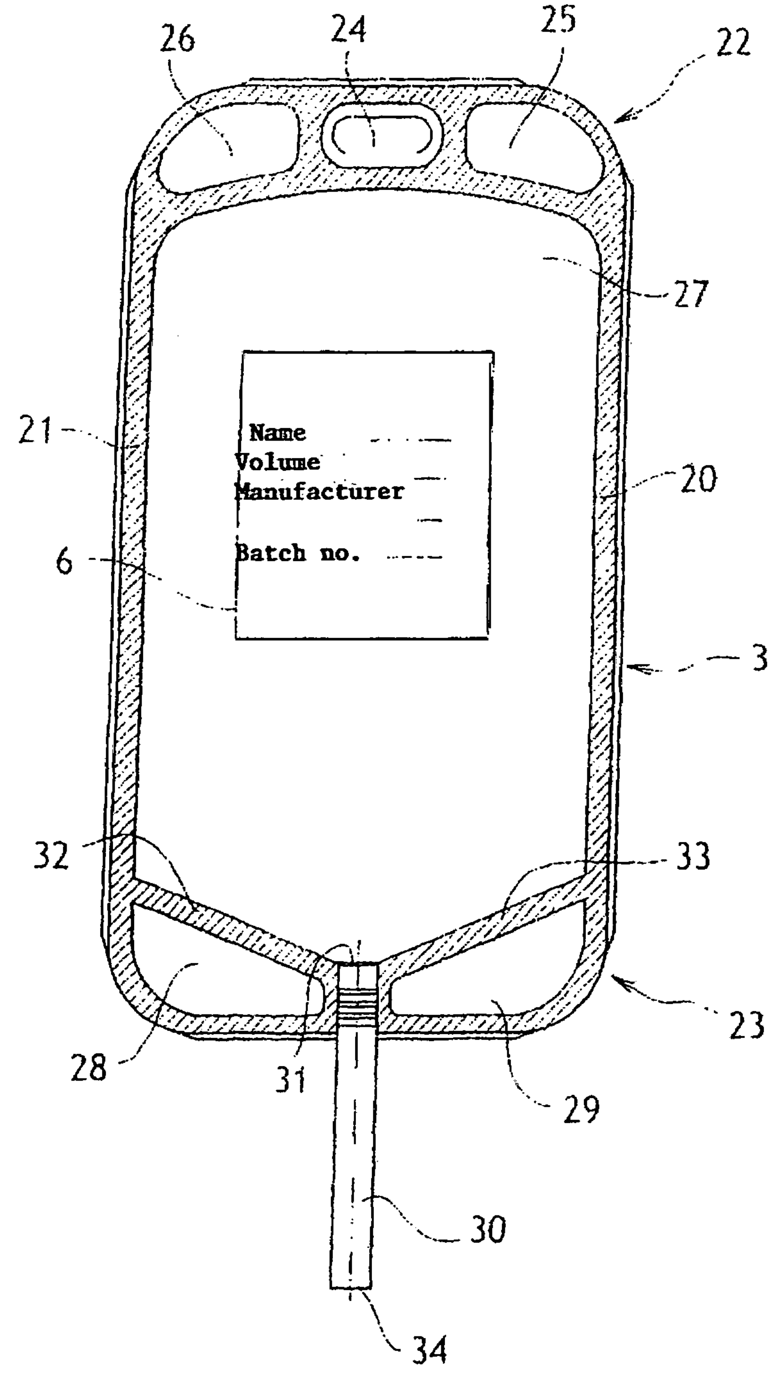
FIG. 5 is a front view of a medical pouch according to the present invention.
Figure 6:
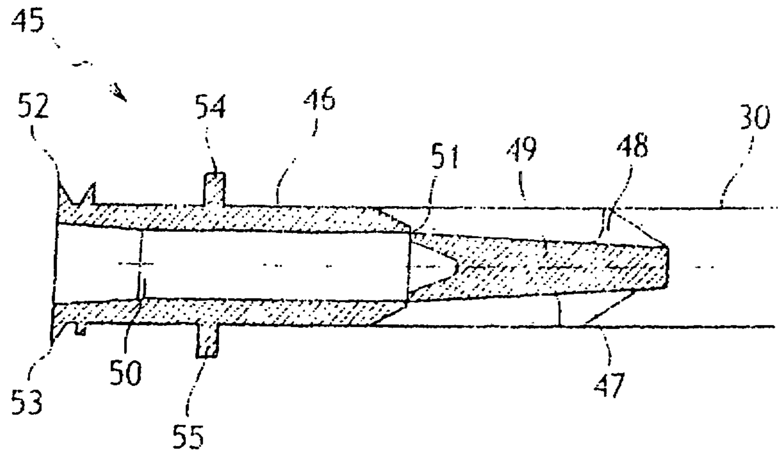
FIG. 6 is an axial sectional view of a female Luer according to the present invention.
Figure 7:
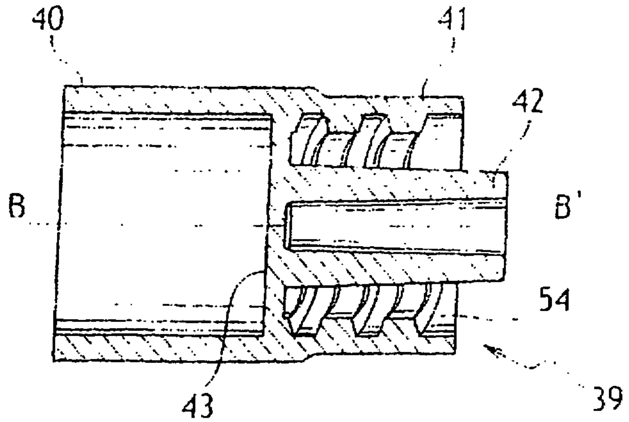
FIG. 7 is an axial sectional view of a cap according to the present invention.
Figure 8:
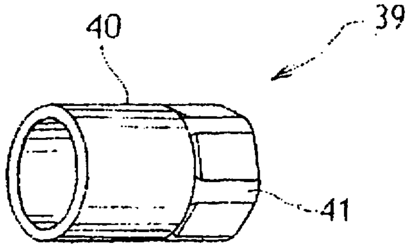
FIG. 8 is a perspective view of the cap of FIG. 7.
Figure 9:
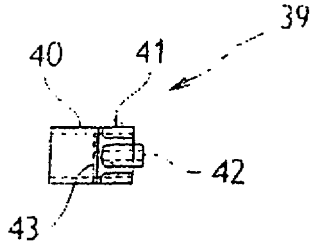
FIG. 9 is another axial sectional view of the cap of FIGS. 7 and 8.
Figure 10:
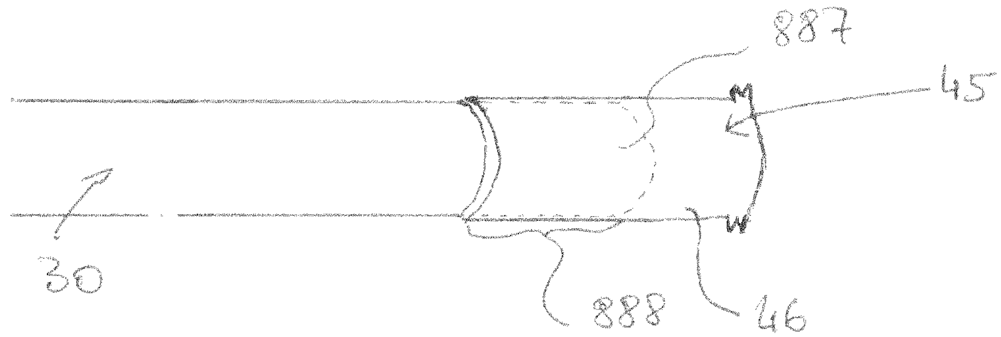
FIGS. 10 and 11 are illustrations of various embodiments of the female Luer according to the invention.
Figure 11:
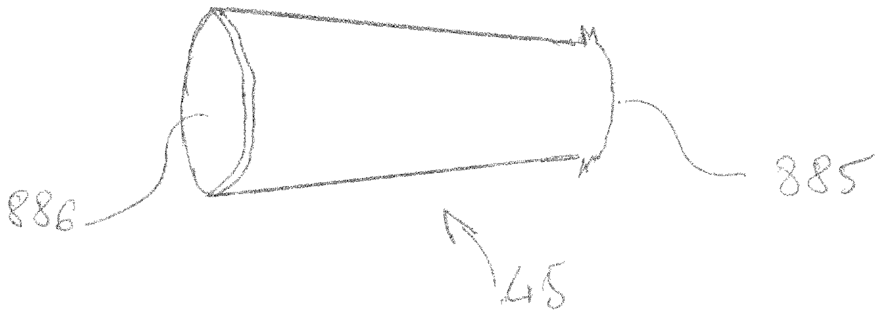

As illustrated in FIG. 5, the superposed sheets 7, 8 forming the medical pouch 3 are sealed along their lateral peripheries 20 and 21 so as to form a pouch 3 with a generally rectangular external appearance. The medical pouch 3 further includes a non-pliant upper part 22 and a non-pliant lower part 23. Finally, the first sheet 7 includes the region 6 bearing the identification inscriptions (name, volume, manufacturer, batch number).

The upper part 22 of the medical pouch 3 comprises a central sector, in which the polymer sheets are sealed together and form a hole 24 of elliptical appearance, for suspending the medical pouch 3 during administration of its contents to the patient, and two symmetrically placed ovoid sectors 25 and 26 extending outwards from the hole 24 and sealed on their periphery in order to make the upper part 22 less flexible than the polymer sheets that form the internal reservoir 27. The rounded shape of the upper part 22 is advantageous, especially when the pouch is used in an automatic injector as described in document EP 852 152, as it makes complete evacuation of the product out of the pouch easier.

The lower part 23 of the medical pouch 3 (where the access member 30 is located) comprises two symmetrically placed sectors 28 and 29 extending outwards from the centre of the medical pouch 3 and sealed on their periphery in order to make the lower part 23 less flexible than the polymer sheets that form the internal reservoir 27.

The internal reservoir 27 of the medical pouch 3 terminates, in its lower part, in two segments 32, 33. Taking the axis of symmetry A-A' of the medical pouch 3 as passing through the centre of the access member 30, the angle between the segment 32 (or segment 33) and the axis of symmetry A-A' makes an angle between 10° and 85°, preferably between 60° and 80° and better still between 67° and 68°. This angle makes it possible to direct and facilitate the flow of the fluid contained in the medical pouch 3 towards the access member 30.

Typically, the dimensions of the medical pouch 3 are the following:

- for a pouch with a volume of 100 ml:
  - width of a sheet between 80 and 120 millimeters (mm), preferably between 97 and 103 mm;
  - length of a sheet between 100 and 200 mm, preferably between 136 and 196 mm;
  - width of the region 6 bearing the identification inscriptions between 35 and 95 mm, preferably about 65 mm; and
  - length of the region 6 bearing the identification inscriptions between 60 and 120 mm, preferably 90 mm;
- for a pouch with a volume of 150 ml:
  - width of a sheet between 80 and 120 mm, preferably between 97 and 103 mm;
  - length of a sheet between 90 and 290 mm, preferably between 160 and 220 mm;
  - width of the region 6 bearing the identification inscriptions between 35 and 95 mm, preferably about 65 mm; and
  - length of the region 6 bearing the identification inscriptions between 85 and 145 mm, preferably 115 mm;
- for a pouch with a volume of 200 ml:
  - width of a sheet between 80 and 120 mm, preferably between 97 and 103 mm;
  - length of a sheet between 100 and 340 mm, preferably between 190 and 250 mm;
  - width of the region 6 bearing the identification inscriptions between 35 and 95 mm, preferably about 65 mm; and
  - length of the region 6 bearing the identification inscriptions between 80 and 200 mm, preferably 140 mm; and
- for a pouch with a volume of 500 ml:
  - width of a sheet between 100 and 160 mm, preferably between 129 and 135 mm;
  - length of a sheet between 150 and 310 mm, preferably between 210 and 270 mm;
  - width of the region 6 bearing the identification inscriptions between 60 and 140 mm, preferably about 97 mm; and
  - length of the region 6 bearing the identification inscriptions between 100 and 200 mm, preferably 150 mm.

The access member 30 is located at the centre of the lower part of the medical pouch 3 and is sealed between the superposed sheets 7, 8. This access member 30 is a tube that may have a multilayer structure, that is to say it may comprise a stack of films. The composition of the external film of the access member 30 is compatible with the internal film of the sheets forming the medical pouch 3 so as to ensure high-quality welding to the sheets forming the pouch. The composition of the internal film of the access member 30 is such that it adheres well to various materials, including polycarbonate materials. For example, the monolayer or multilayer tube comprises a polypropylene ethylenelpolyethylene-vinyl acetate/styrene blend.

The access member 30 is used for filling the pouch 3 with the parenteral fluid and for administering this fluid to the patient. It is very advantageous for the proximal end 31 of the access member 30 coming into contact with the medical fluid to be flush or just below a horizontal plane intersecting the centre of the lower part of the internal reservoir so that the entire liquid contents can flow out of the medical pouch 3. However, a tolerance may be introduced by which the tube is inserted, thus allowing the tube to extend therebeyond.

The dimensions of the access member 30 are typically the following:

- length of the access member between 30 and 70 mm, preferably between 53 and 61 mm;
- inside diameter between 5.8 and 6.4 mm, preferably about 6.1 mm; and
- outside diameter between 7.8 and 8.4 mm, preferably 8.1 mm.

The Luer (Or Luer Lock):

After the pouch 3 has been filled with the parenteral solution, the access member 30 is sealed with a frangible female Luer 45 (made of polycarbonate) on which a cap 39 is placed. This Luer 45 and this cap 39 are for example made of bisphenol A polycarbonate.

The cap 39 comprises a cylindrical body 40 extended at one of its ends by a ferrule 42.

The cylindrical body 40 includes a blind opening at its end furthest away from the ferrule 41. At the centre of the ferrule 41 there is a coaxial tubular part 42 projecting slightly from the ferrule 41. The tubular part 42 and the cylindrical body 40 are separated by a circular wall 43 orthogonal to the axis of symmetry B-B' of a cap 39.

The female Luer connector 45 comprises a cylindrical body 46 extended, at one end, by a frangible section 49. When the female Luer connector 45 is engaged with the access member 30 of the medical pouch 3, the frangible part 49 lies inside the access member.

The frangible section 49 includes four fins 47, 48 extending radially outwards so that when the female Luer 45 is engaged with the access member 30 the ends of the fins 47, 48 are in contact with the access member 30. These fins allow the frangible section 49 to be separated more easily by the user. The four fins 47, 48 are arranged so that one fin is perpendicular to the two neighbouring fins.

The cylindrical body 46 has a central passage 50 terminating, on the same side as the frangible section 49, near a thin bridging rupture element 51. At its other end, the passage 50 is open and its diameter corresponds to the outside diameter of the tubular part 42 of the cap 39. The female Luer 45 is able to engage in the ferrule 41 of the cap 39, the tubular part 42 of the cap 39 being engaged in the passage 50.

The cylindrical body 46 is provided externally, on the opposite side from the frangible section 49, with two opposed threaded sections 52, 53 that cooperate with the thread 54 of the ferrule 41 of the cap 39 so as to couple the cap 39 and the female Luer 45 by screwing. Each threaded section 52, 53 includes two lugs extending radially outwards and making an angle of approximately 50° between them.

Advantageously, the external wall of the tubular part 42 is slightly conical so as to seal the connection.

The female Luer 45 used to seal the medical pouch 3 has the benefit of being a connection system that can be fitted directly onto a syringe, and is therefore very simple to use.

After the pouch 3 has been filled, the female Luer 45 is engaged with the access member 30, the frangible section 49 being inside the access member 30, the distal end 34 of which (i.e. distal relative to the pouch 3), forcibly engaged on the cylindrical body 46, butts against two protuberances 54, 55. Sealing between the female Luer 45 and the access member 30 is achieved thanks to the bisphenol A polycarbonate of which the female Luer 45 is made. This is because bisphenol A polycarbonate adheres to the access member 30 during the phase of sterilizing the medical pouch 3.

The dimensions of the female Luer 45 are typically the following:

- diameter of the central passage 50 between 3.5 mm and 4.1 mm, preferably about 3.8 mm;
- outside diameter of the cylindrical body 46 between 6 mm and 7 mm, preferably about 6.5 mm;
- distance between the ends of the protuberances 54, 55 about 10 mm;
- length of the female Luer 45 (with the frangible section 49) between 30 mm and 50 mm, preferably between 36 mm and 37.4 mm; and
- length of the frangible section 49 between 14 mm and 17 mm, preferably 15.8 mm.

In one embodiment, the cylindrical body 46 of the connector 45 has an outside diameter approximately equal to the inside diameter of the access member 30 so that a portion of the access member 30 encircles and comes into contact with a portion of the cylindrical body 40 when the connector is engaged with the access member 30.

In another embodiment, the cylindrical body 46 of the connector 45 has an inside diameter approximately equal to the outside diameter of the access member 30 so that a portion 888 of the cylindrical body 46 encircles and comes into contact with a portion 887 of the access member 30 when the connector 45 is engaged with the access member 30.

In other words, the cylindrical body 46 of the connector 45 defines an internal space that can receive a portion 887 of the access member 30 when the connector 45 is engaged with the access member 30. This embodiment (access member encircling the connector) is particularly suitable for use with an automatic injector (which will be described in detail later in the rest of the present application). Specifically, this embodiment (access member encircling the connector) prevents leaks liable to occur under the effect of the pressure at the connection between the connector 45 and the access member 30.

In another embodiment, the cylindrical body 46 of the connector 45 has an external surface in the form of part of a truncated cone, the diameter of which decreases from the proximal end 886 towards the distal end 885 of the cylindrical body 46. This makes it easier to insert the access member into the internal space of the cylindrical body.

Within the context of the present invention, the term "proximal end" is understood to mean the end closest to the access member when the connector and the access member are engaged, one with the other.

Thus, the assembly for storing a parenteral solution comprises an overpouch 4, a medical pouch 3, a female Luer 45 and a cap 39. The female Luer variant described is not limiting, as other structures may be appropriate.

A method for storing the parenteral solution will now be described.

Contrary to the systems and methods of the prior art, the present storage method provides a storage assembly that is very effective and easy to use, allowing the user to easily administer the parenteral solution contained in the storage assembly to a patient.

The first step of the method consists in manufacturing the pouch 3 and the overpouch 4.

To manufacture the pouch 3, the access member 30 is placed between two laminated sheets 7, 8 of the type described above, and the two laminated sheets 7, 8 and the access member 30 are welded together. Next, the inscriptions for identifying the parenteral solution are printed on the region 6. The pouch 3 is then ready for the filling operation.

To manufacture the overpouch 4, the first foil 1 left transparent and the second foil 2 comprising an opaque laminated film are superposed. Three of the four marginal edges 11, 12, 13 of the superposed foils 1, 2 are then welded together, typically be thermal welding. The overpouch 4 is then ready to receive the medical pouch 3.

The second step of the method (which may of course take place long after the first step of the method, the pouches being stored empty) consists in filling the pouch 3 with the parenteral solution, in plugging it with the female Luer 45 and the cap 39, and in sterilizing the medical pouch 3.

To fill the medical pouch 3, the access member 30 (a tube) is used. Once the sufficient amount of parenteral solution has been introduced into the pouch 3, the female Luer 45 is forcibly fitted to the access member 30, frangible part 49 towards the inside of the access member 30, so as to close it. Next, the cap 39 is screwed onto the female Luer 45. Finally, the device composed of the pouch 3 containing the parenteral solution, the access member 30, the female Luer 45 and the cap 39 is placed in an autoclave at about 121° C. for about 20 minutes so as to sterilize said device. During this sterilization phase, the female Luer 45 and the access member 30 adhere to each other owing to the heat. Thus it is possible to produce the sealed joint thermally before the sterilization. This avoids any risk of a leak at the female Luer 45. Once the sterilization is complete, the device is ready to be placed in the overpouch 4.

The last step of the method consists in placing in the overpouch 4 the pouch 3 containing the parenteral solution and comprising the access member 30 on which the female Luer 45 provided with the cap 39 is placed. This medical pouch 3 is placed in the overpouch 4 so that the region 6 bearing the identification inscriptions is in contact with the inner face of the first foil 1 left transparent. Once the medical pouch 3 has been placed in the overpouch 4, the last edge of the overpouch 4 is welded.

In one embodiment the Luer is mounted already plugged, and not plugged after fitting the Luer onto the pouch.

The storage assembly 5 according to the invention is then ready for use.

It should be noted that, contrary to the methods of the prior art once the pouch 3 has been placed in the overpouch 4, the storage assembly 5 according to the invention, comprising the overpouch 4, the pouch 3, the access member 30, the female Luer 45 and the cap 39, is not sterilized again.

The storage assembly thus obtained can then be stored, in secondary packaging of the cardboard box type. It is recommended that the clinical user preferably store the assembly with the opaque face towards the top of the packaging assembly, so that the translucent face of the overpouch receives the minimum amount of light.

The advantages and the ease of use of the storage assembly will have been understood from the description. For example, once the pouch has been removed from the overpouch, a connection system will be used that comprises a flexible adapter having at one end a male part intended to cooperate with the female Luer of the pouch, and at the other end a male or female part able to be connected in particular:

- to an injection syringe, for manual injection, or to an inlet of an automatic syringe injector;
- to an outlet tube of an automatic injector for pouches: the contrast agent is thus discharged from the pouch automatically by programming the injector, via the adapter, to a device for administering it to the patient.

In a highly advantageous embodiment, the injector is a one-piece injector and it contains a chamber as described in document EP 852 152. In particular, an injector allowing substantially complete discharge of the contrast agent will be preferred, so as to limit any product loss. A solid sleeve under the effect of a pressurized fluid is applied against the foils of the pouch, the content of which is then discharged towards the patient. Preferably, the rate of discharge is controlled: about 5 ml/second for a product in solution for X-ray analysis or MRI; 10 to 100 times less for a contrast agent in suspension, consisting of iron oxide particles. Large volumes, for example 500 ml, allow several patients to be treated "in series". The injector may receive several pouches depending on the clinical use requirements, for example one injector may receive several pouches of the same content or different content (contrast agent, physiological serum, etc.). It is also possible to combine, in one injector, a small-volume (20 ml for example) pouch of contrast agent with for example a 100 ml pouch. The pouches within one and the same injector may be connected to a different discharge line with a possibly different administration sequence between the products, or to a common discharge line with a Y-system.

It is also possible to provide a pouch having several access points. For example, the pouch contains an output tube offset with respect to the axis of symmetry, and at least one reclosable tube for injection into the pouch. Thus, the composition of the content of a partially emptied pouch in which it is desired to introduce a compound, such as an additive or a dilution or stabilization buffer, may be adjusted. This may be useful in particular for products that might give rise to crystallization problems.

It is also possible to provide reinforcing means, where appropriate to adjust the shape of the overpouch so that the packaging assembly stands upright without falling over.

The reader will have understood that many modifications may be made without materially departing from the novel teachings and advantages described here. Consequently, all modifications of this type are intended to be incorporated within the scope of the system and of the method of displaying regions of interest as defined in the appended claims. For example, the storage method described can be adapted for pouches whose structure differs from that of the packaging containers by having another shape and/or having different discharge means.

The invention claimed is:

1. A doubly packaged storage assembly for an aqueous medical solution, comprising an overpackage wherein a flexible packaging container is packaged and hermetically sealed, said container being filled with an aqueous solution and sealed by means of a connector provided with a cap, wherein:

- the overpackage comprises two superposed foils made of flexible or semi-rigid polymer materials, the first foil being transparent over its entire area and the second foil being opaque over its entire area; said foils having a thickness between 50 μm and 100 μm; said foils being made of polyamide, polyethylene, polypropylene, or polyethylene/polypropylene copolymer, wherein the first foil comprises laminated film selected from the group of polypropylene film, polyamide film and polyethylene film and the second foil comprises an opaque aluminium film, so that a loss of aqueous solution contained in the storage assembly is 1% or less for 36 months,
- the packaging container comprises two superposed sheets made of polymer material comprising polyethylene and/or polypropylene and an access member at the distal end of which the connector and the cap are placed, the connector allowing the packaging container to be sealed after it has been filled with the aqueous solution, and
- the connector comprises a cylindrical body, one inside diameter of which is approximately equal to the outside diameter of the access member so that a portion of the cylindrical body encircles and comes into contact with a portion of the access member when the connector is engaged with the access member.

2. The storage assembly according to claim 1, wherein that the connector and the cap are made of polycarbonate.

3. The storage assembly according to claim 1, wherein the connector has an external surface in the form of part of a truncated cone.

4. The storage assembly according to claim 3, wherein the diameter of the external surface in the form of a truncated cone decreases from the proximal end towards the distal end of the cylindrical body.

5. The storage assembly according to claim 1, wherein the connector is of the female Luer type.

6. The storage assembly according to claim 1, wherein the connector includes a frangible section provided with fins extending radially outwards.

7. The storage assembly according to claim 1, wherein the foils of the overpackage are composed of laminated films chosen from polypropylene, polyamide and polyethylene films.

8. The storage assembly according to claim 1, wherein the second foil of the overpackage comprises an opaque film of the metallized polyester type.

9. The storage assembly according to claim 1, wherein the second foil of the overpackage comprises an opaque aluminium film.

10. The storage assembly according to claim 1, wherein the sheets of the packaging container are composed of laminated polypropylene films.

11. The storage assembly according to claim 1, wherein the first sheet includes a region having an identification inscription.

12. The storage assembly according to claim 1, wherein the superposed sheets sealed on their periphery define an internal reservoir, the upper part of the packaging container comprising a central sector, in which the sheets are sealed together and form a hole of elliptical appearance, and two symmetrically placed ovoid sectors extending outwards from the hole and sealed on their periphery in order to make the upper part less flexible than the polymer sheets that form the internal reservoir.

13. The storage assembly according to claim 1, wherein the superposed sheets sealed on their periphery define an internal reservoir, the lower part of the packaging container comprising two symmetrically placed ovoid sectors extending outwards from the hole and sealed on their periphery in order to make the lower part less flexible than the polymer sheets that form the internal reservoir.

14. A method of storing an aqueous medical solution in a doubly packaged storage assembly, wherein said method comprises the steps of:

filling a packaging container with the aqueous medical solution via an access member of the packaging container;

sealing the packaging container by means of a connector;

placing a cap on the end of the connector to obtain a tight link between the cap and the connector to thereby form an assembly of the packaging container, connector, access member and cap of the connector;

placing the packaging container, the access member of which is sealed by the connector, in an overpackage;

sealing the overpackage so as to hermetically seal the container, the access member of which is sealed by the connector provided with the cap, and sterilizing the assembly comprising the packaging container, the connector, the access member and the cap of the connector, prior to the step of placing the packaging container in the overpackage, wherein once the assembly is placed in the overpackage it is not sterilized again, the overpackage comprises two superposed foils made of flexible or semi-rigid polymer materials, the first foil being transparent over its entire area and the second foil being opaque over its entire area, wherein the first foil comprises laminated film selected from the group of polypropylene film, polyamide film and polyethylene film and the second foil comprises an opaque aluminium film, so that a loss of aqueous solution contained in the storage assembly is 1% or less for 36 months, and the connector comprises a cylindrical body, one inside diameter of which is approximately equal to the outside diameter of the access member so that a portion of the cylindrical body encircles and comes into contact with a portion of the access member when the connector is engaged with the access member.

15. The storage method according to claim 14, wherein the connector is a female Luer connector.

16. The storage method according to claim 14, further comprising the step of, prior to the step of placing the container in the overpackage, sterilizing the assembly comprising the packaging container, the connector and the cap by autoclaving at a temperature of approximately 121° C. for a time of approximately 20 minutes.

17. The storage assembly according to claim 1, wherein the aqueous medical solution is a contrast agent.

18. The storage assembly according to claim 11, wherein the identification inscription is a name of a product, a name of a manufacturer or an amount of a product contained in the container.

19. The storage method according to claim 14, wherein the step of sterilizing the assembly is conducted by autoclaving between 100 and 150° C. for a time between 10 and 40 minutes.

20. The storage assembly according to claim 1, wherein the foils of the overpackage have a thickness between 60 μm and 75 μm.

21. The storage assembly according to claim 20, wherein the foils of the overpackage have a thickness between 62 μm and 71 μm.

22. The storage assembly according to claim 20, wherein the foils of the overpackage have a weight between 64.90 $g/m^2$ and 92.20 $g/m^2$.

23. The storage assembly according to claim 1, wherein the foils of the overpackage are made of a material chosen from the group consisting of polyamide, polyethylene, polypropylene and polyethylene/polypropylene copolymer.

24. The storage assembly according to claim 1, wherein the overpackage is disposed so as to prevent both loss of water in the packaging container and condensation inside the overpackage.

25. The storage method according to claim 14, further comprising the step of storing the packaged storage assembly so that the second opaque foil faces upwardly so as to minimize amount of light the first transparent foil receives.

* * * * *